United States Patent [19]

Roane

[11] 4,443,193

[45] Apr. 17, 1984

[54] ENDODONTIC INSTRUMENT

[76] Inventor: James B. Roane, 707 SW. 24th St., Norman, Okla. 73069

[21] Appl. No.: 464,972

[22] Filed: Feb. 8, 1983

[51] Int. Cl.³ .............................................. A61C 5/04
[52] U.S. Cl. .................................................. 433/102
[58] Field of Search ......................... 433/102, 122, 81

[56] References Cited

U.S. PATENT DOCUMENTS

| D. 250,544 | 12/1978 | Leonard | 433/102 |
|---|---|---|---|
| 273,821 | 3/1883 | Crosthwaite | 433/102 |
| 444,383 | 1/1891 | Ivory | 433/102 |
| 498,554 | 5/1893 | Johanson | 433/102 |
| 717,594 | 1/1903 | Miles, Jr. | 433/102 |
| 1,067,015 | 7/1913 | Fowler | 433/102 |
| 1,307,446 | 6/1919 | Kerr | 433/102 |
| 1,844,913 | 2/1932 | Hallowell | 433/102 |
| 2,677,843 | 5/1954 | Goodman | 433/102 |
| 3,388,473 | 6/1968 | Loran | 433/102 |
| 3,562,913 | 2/1971 | Saffro | 433/102 |
| 3,713,221 | 1/1973 | Malmin | 433/102 |
| 3,772,791 | 11/1973 | Malmin | 433/102 |
| 3,781,996 | 1/1974 | Saffro | 433/102 |
| 4,019,254 | 4/1977 | Malmin | 433/102 |
| 4,028,810 | 6/1977 | Vice | 433/102 |
| 4,165,562 | 8/1979 | Sarfatti | 433/102 |
| 4,190,958 | 3/1980 | Martin et al. | 433/102 |
| 4,260,379 | 4/1981 | Groves et al. | 433/102 |
| 4,268,251 | 5/1981 | Takasugi et al. | 433/102 |
| 4,280,808 | 7/1981 | Johnsen et al. | 433/102 |
| 4,299,571 | 11/1981 | McSpadden | 433/102 |
| 4,332,561 | 6/1982 | McSpadden | 433/102 |
| 4,340,364 | 7/1982 | Deemer | 433/102 |
| 4,353,698 | 10/1982 | McSpadden | 433/102 |

OTHER PUBLICATIONS

Brochure of Unitek Corporation entitled "Unitek's New Generation Endodontic Files and Reamers", 1980.
Endodontics, Second Edition, John Ide Ingle, D.D.S., M.S.D., and Edward Edgerton Beveridge, D.D.S., M.S.D., pp. 168-215 (1976).
Franklin S. Weine, D.D.S., M.S.D.; Robert F. Kelly, D.D.S.; and Peter J. Lio, D.D.S., M.S., Maywood, Illinois, Journal of Endodontics, "The Effect of Preparation Procedures on Original Canal Shape and on Apical Foramen Shape", vol. 1, No. 8, Aug. 1975, pp. 255-262.
Franklin S. Weine, D.D.S., M.S.D.; Robert F. Kelly, D.D.S.; and Kenneth E. Bray, D.D.S., M.S., Maywood, Illinois, Journal of Endodontics, "Effect of Preparation with Endodontic Handpieces on Original Canal Shape", vol. 2, No. 10, Oct. 1976, pp. 298-303.
Exhibit A, Photograph of Unitek Brand Size 70 File.
Exhibit B, Photograph of Kerr Brand Size 70 File.
Exhibit C, Photograph of Star Brand Size 25 File.
Exhibit D, Photograph of Star Brand Size 70 File.
Exhibit E, Photograph of Star Brand Size 40 Reamer.
Exhibit F, Photograph of Star Brand Size 70 Reamer.
Exhibit G, Photograph of Union Broach Brand Size 55 File.
Exhibit H, Photograph of Healthco Brand Size 35 File.
Exhibit I, Photograph of Hygenic Brand Size 35 File.
Exhibit J, Photograph of Kerr K-Flex Brand Size 70 File.
Exhibit K, Photograph of Union Broach Brand Size 80 File.
Exhibit L, Photograph of Burns Unifile Brand Size 60 File.

Primary Examiner—Robert Peshock
Attorney, Agent, or Firm—Laney, Dougherty, Hessin & Beavers

[57] ABSTRACT

An improved endodontic instrument includes a tapered working portion defined on a flexible shaft. The working portion includes a plurality of spiral rotationally bi-directional cutting edges thereon. The instrument includes a tapered tip defined on the flexible shaft and intersecting an end of each of the cutting edges of the working portion. The tapered tip has a greater angle of taper than does the tapered working portion. The tapered tip is shaped such that the sharp cutting points which are normally present at an intersection between the ends of the cutting edges and a standard 75° included angle conically tapered tip are substantially eliminated so that lateral transportation of the instrument when cutting a curved root canal is reduced as compared to an otherwise similar instrument having a standard 75° included angle conically tapered tip.

28 Claims, 9 Drawing Figures

ENDODONTIC INSTRUMENT

BACKGROUND OF THE INVENTION

1. Field Of The Invention

The present invention relates to endodontic instruments such as files and reamers.

2. Description Of The Prior Art

The field of endodontics involves the cleaning and enlargement of the root canals of human teeth for the purpose of removing organic material and extraneous material present in the root canal, and for enlarging the root canal so that it may be filled.

To perform such an operation, an opening is cut in the upper part of the tooth to open up the hollow portion of the tooth, and small endodontic instruments are utilized to then clean and enlarge the long narrow tapered root canals.

One very commonly used such instrument is known as a K-type file and is constructed by axially twisting a tapered triangular cross-section shaft to form three spiral cutting edges along the tapered portion of the shaft. A K-type file normally has a conical shaped tapered tip ground on the end thereof, which in accordance with standards set up by the American Dental Association and other standardizing bodies has an included angle of 75° with an allowable tolerance of plus or minus 15°. At the intersection of this standard 75° included angle conically tapered tip with the ends of the three spiral cutting edges, relatively sharp points are created which extend laterally from the axis of the endodontic instrument.

While these standard K-type files perform entirely satisfactorily when cleaning and enlarging a straight root canal, a serious problem is often encountered when using such files to clean and enlarge a curved root canal.

As will be understood by those skilled in the art, a very large portion of the root canals encountered by a practicing endodontist are of the curved variety, and thus this problem is a significant one for the profession.

When cleaning and enlarging a root canal, the operation is performed using a set of similar endodontic files of sequentially increasing diameter. Typically an operation is begun with a file having an outside diameter at its smaller end of 0.25 millimeters. The subsequently used instruments have diameters of 0.30, 0.35, 0.40, 0.45, 0.50, 0.55, and 0.60 millimeters. Still further instruments are available with diameters increasing in steps of 0.10 millimeter up to 1.40 millimeters for the largest size in common usage. Also, some smaller instruments are available which are sometimes used, and which have diameters of 0.10, 0.15 and 0.20 millimeters. File sizes correspond to diameter, and thus a No. 25 file has an outside diameter at its smaller end of 0.25 millimeters.

When performing an operation on a curved root canal, the operation is begun utilizing one of the smaller diameter files, such as for example a 0.25 millimeter instrument. This small diameter instrument is relatively flexible and can easily be inserted into the canal and will easily bend to fit the curved shape of the canal. With increasingly larger sizes of instruments, however, the instrument becomes significantly less flexible and becomes more and more difficult to insert through the curved portion of the canal. When utilizing the instrument to enlarge the curved portion of the canal, the force exerted along the axially outermost portion of the instrument against the root canal is very much greater against that part of the root canal to the outside of the curvature than it is against that part of the root canal on the inside of the curvature. Indeed, in many cases, the instrument will cut only on the outside of the curve and will not cut on the inside of the curvature of the root canal along those portions of the root canal near the apex.

Thus, when this problem is first encountered, the instrument being utilized will tend to cut a ledge along the outside of the curvature of the root canal at the forwardmost point in the root canal which is reached by the instrument. The succeeding instruments of greater diameter then encounter even more difficulty in conforming to the curved shaped of the canal, since it is difficult and sometimes impossible to move the tip of the next larger instrument past the ledge created by the previous instrument. Accordingly, the ledge on the outside of the curvature of the root canal is enlarged by each successively larger instrument, and ultimately the instruments very much enlarge the root canal at the point of forwardmost extent of the instruments, and in severe cases the instruments may even perforate the side of the tooth causing serious consequences for the patient.

The problem just described is often referred to as "transportation" of the instrument tip, since the tip is transported or moves laterally away from the original root canal.

This problem of transportation is also present to some extent in endodontic instruments other than the standard K-type instrument, although it is generally most severe with the K-type instrument. For example, this problem of transportation is also encountered utilizing a Hedstrom instrument which is constructed by machining one or two cutting grooves in a round tapered shaft. The Hedstrom instrument differs substantially from the K-type instrument in that the Hedstrom instrument can only cut in a single rotational direction, whereas the K-type instrument has spiral cutting edges which are rotationally bi-directional in that they may cut when rotated either clockwise or counterclockwise.

Although the prior art has appreciated the fact that transportation does occur when using endodontic instruments, and it is known that this is a serious problem which many persons have tried for a long period of time to correct, it is not believed that prior to the present invention anyone has appreciated the primary cause of lateral transportation in a K-type instrument.

SUMMARY OF THE INVENTION

The present invention provides an improved construction for K-type files and for all files having a plurality of spiral rotationally bi-directional cutting edges formed by axially twisting a polygonal cross-section shaft.

I have determined that the primary cause of lateral transportation when utilizing a K-type endodontic instrument to clean and enlarge a curved root canal is the presence of the sharp points which are normally present on a standard K-type instrument which has a 75° included angle conically tapered tip intersecting the ends of the spiral cutting edges.

By removing these sharp points, the high stress concentration previously created where the points engaged the tooth material is eliminated and the forces exerted by the axially forwardmost part of the instrument against the wall of the root canal is spread over a much greater area of the tooth material and no sharp ledges are created.

This improvement is provided by forming a tapered tip on the endodontic instrument which is shaped so as to eliminate the sharp points present in a standard K-type instrument having a standard 75° included angle conically tapered tip.

In a preferred embodiment of the invention, the tapered tip includes an axially outermost tapered portion which is substantially conical in shape and has an included angle in the range of 60° to 90°, and includes an axially innermost tapered portion which is substantially frusto-conical in shape and has an included angle of substantially less than 75°.

It is therefore a general object of the present invention to provide an improved endodontic instrument which minimizes lateral transportation when cleaning and enlarging a curved root canal. Another object of the present invention is the provision of methods of using and of manufacturing such an improved endodontic instrument.

Other and further objects, features and advantages of the present invention will be readily apparent to those skilled in the art upon a reading of the following disclosure when taken in conjunction with the accompanying drawings.

DETAILED DESCRIPTION OF THE PREFERRED EMBODIMENT

Figure 1:
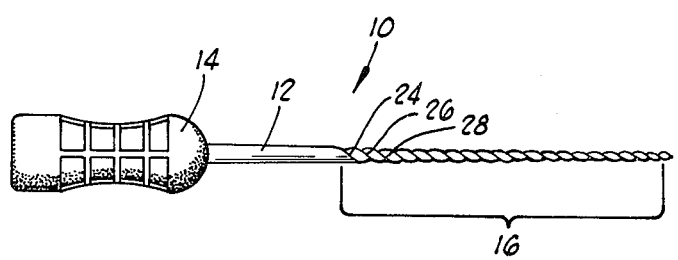
FIG. 1 illustrates a typical prior art K-type endodontic file constructed to be held by a dentist between the thumb and forefinger of one hand.

Referring now to FIG. 1, a typical prior art K-type file is there illustrated and designated by the numeral 10. The file 10 includes a flexible tapered shaft 12 which has a handle 14 attached to one end thereof. The handle 14 is constructed to be grasped by the dentist between the thumb and forefinger of one hand.

The shaft 12 has a working portion 16 formed thereon by axially twisting the shaft.

Figure 5:
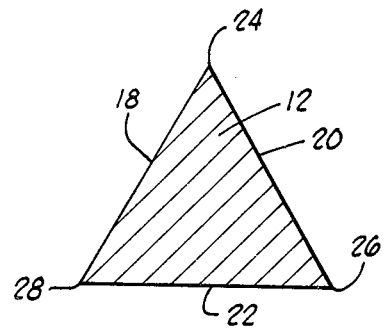
FIG. 5 is a cross-sectional view of a blank shaft of the type used to construct a standard K-type file, prior to the axial twisting of that shaft to form the spiral cutting edges.
Figure 6:
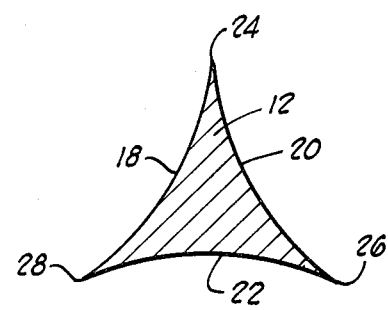
FIG. 6 is a sectional view of a standard K-type file after the same is axially twisted. The twisting of the shaft causes the sides of the triangular cross-section to become somewhat concave.

Prior to axially twisting the working portion 16 of shaft 12, that working portion of the blank shaft, i.e., the untwisted shaft, has a polygonal shaped cross-section which preferably is shaped as an equilateral triangle as seen in FIG. 5. After twisting of the working portion of the shaft to the configuration shown in FIG. 1, a cross-section of the working portion of the shaft appears somewhat as schematically shown in FIG. 6 wherein the sides 18, 20 and 22 have become somewhat concave due to the deformation of the shaft as it is twisted. In the following disclosure the shape after twisting, such as schematically illustrated in FIG. 6, is referred to as being generally polygonal in shape, recognizing that the sides are slightly deformed from a true polygonal shape.

The sides 18, 20 and 22 of the shaft 12 join at sharp edges 24, 26 and 28. After the working portion 16 of shaft 12 has been twisted to the form shown in FIG. 1, the edges 24, 26 and 28 are in the form of spirals.

The spiral shaped edges 24, 26 and 28 may be referred to as spiral rotationally bi-directional cutting edges, since the edges 24, 26 and 28 will cut when the shaft 12 is rotated in either a clockwise or counterclockwise direction.

This is in contrast to another very commonly used file known as a Hedstrom file. The Hedstrom file has one or more spiral grooves machined in a round tapered shaft to form a rotationally uni-directional cutting edge.

For the purposes of this disclosure these two most commonly used types of endodontic instruments, K-type and Hedstrom type, are being classified as having rotationally bi-directional and rotationally uni-directional spiral cutting edges, respectively, in order to distinguish between them. The present invention applies only to instruments having rotationally bi-directional cutting edges, because the particular manner in which those instruments are constructed as described above creates the sharp laterally extending points which cause lateral transportation. Those persons skilled in the art will understand, however, that either of these types of instruments can be and often are utilized by axially reciprocating the instrument in the root canal to cut the tooth material, rather than by rotational cutting motion.

The term rotationally bi-directional is used only to describe the type of cutting edge the instrument has, and in no way limits the present invention to instruments used solely with a rotational cutting stroke. The improved endodontic instrument of the present invention may be utilized, and its benefits received, with either a rotational or an axial cutting stroke. As set forth in more detail below, however, a particular type of rotational cutting stroke has been determined to be the preferred manner of using the improved endodontic instrument of the present invention.

Figures 2, 3, 4:
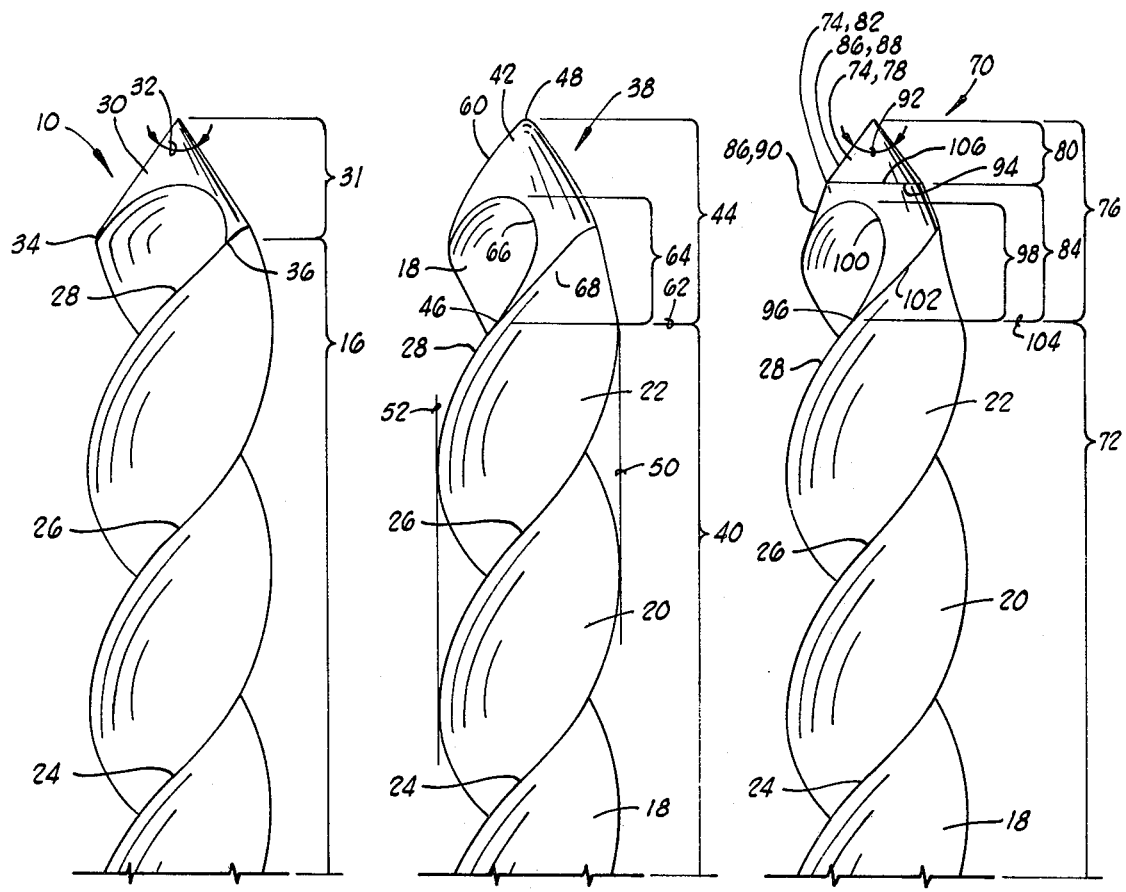
FIG. 2 is a very much enlarged illustration of the axially outermost portion of the prior art K-type file having a standard 75° included angle conically tapered tip thereon.
FIG. 3 illustrates an endodontic instrument having a tapered tip constructed in accordance with the present invention, which tapered tip has a continuously curved profile of rotation.
FIG. 4 illustrates an alternative embodiment of the tapered tip of the endodontic instrument of the present invention which has an axially outermost conically tapered portion and an axially innermost frusto-conically shaped portion.

Referring now to FIG. 2, a very much enlarged view is there shown of the axially forwardmost portion of a standard prior art K-type file 10. The file 10 includes a tapered tip 30 which has a length 31 and an included angle 32. In accordance with standards set out by the American Dental Association and other standardizing bodies as are recited for example in Ingle and Beveridge, Endodontics, Second Edition, pages 174–175 (1976), the included angle 32 is required to be 75° with an allowable tolerance of plus or minus 15°, i.e., in the range of 60° to 90°.

As is seen in FIG. 2, the standard K-type file 10 has three sharp cutting points, two of which are seen in FIG. 2 and designated 34 and 36, at the intersection between the ends of the cutting edges 24, 26 and 28 with the standard 75° included angle conically tapered tip 30.

In FIG. 2, the sharp point 34 is shown substantially in profile and it is apparent that this provides a sharp gouging point which can cut into the tooth material of a root canal.

Referring now to FIG. 3, a first embodiment of the improved endodontic instrument of the present invention is there illustrated and designated by the numeral 38. Only the axially forwardmost portion of the shaft of the endodontic instrument 38 is illustrated in FIG. 3, it being understood that the portions of the endodontic instrument 38 other than the tapered tip are identical to the prior art endodontic instrument 10 just described.

The endodontic instrument 38 includes a tapered working portion, the axially forwardmost part of which is shown in FIG. 3 and designated by the numeral 40. The working portion 40 includes the three spiral rotationally bi-directional cutting edges 24, 26 and 28 previously described.

The instrument 38 further includes a tapered tip 42 having a length 44 extending from the ends of the cutting edges, such as end 46 of cutting edge 28, to the axially forwardmost end 48 of the tapered tip 42. The tapered tip 42 intersects the ends, such as end 46, of the cutting edges 24, 26 and 28 of working portion 40.

As is readily apparent in FIG. 3, the tapered tip 42 has a much greater angle of taper than does the tapered working portion 40. The angle of taper of the tapered working portion 40 is defined as the included angle between imaginary lines such as 50 and 52 which define the outside diameter of the working portion 40. In accordance with the previously mentioned standards set forth by the American Dental Association and other standardizing bodies, the taper of the working portion 40 of the shaft must be dimensioned such that there is a gain in diameter of 0.02 millimeter per millimeter of length of the working portion 40.

The angle of taper of the tapered tip 42 is defined as the included angle between lines tangent to two diametically opposed sides of the tapered tip 42 at any point along its length.

Thus it is seen that the angle of taper of the tapered tip 42 is greater than the angle of taper of the tapered working portion 40.

The tapered tip 42 is shaped such that the sharp cutting points, such as 34 and 36 which are normally present at the intersection between the ends of the cutting edges 24, 26 and 28 and a standard 75° included angle conically tapered tip such as the tip 30 shown in FIG. 2, are substantially eliminated so that lateral transportation of the improved endodontic instrument 38 when cutting a curved root canal is reduced as compared to an otherwise similar instrument such as the instrument 10 illustrated in FIG. 2.

Preferably, the tapered tip 42 is continuously tapered from the forwardmost end 48 thereof to the ends, such as 46, of the cutting edges 24, 26 and 28.

Figure 7:
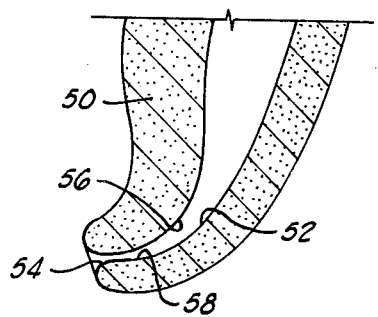
FIG. 7 is a cross-section elevation somewhat schematic view of a human tooth having a curved root canal, prior to the cleaning and enlargement of the root canal.

Referring now to FIG. 7, a cross-section elevation somewhat schematic view is there shown of a root portion 50 of a human tooth having an elongated tapered root canal 52 disposed therein. The root canal 52 typically tapers to an apex 54 which is also referred to as the apical opening or apical foramen of the root canal 52. The root 50 illustrated in FIG. 7 is shown in its natural state prior to any operation thereon. It is seen that the root canal 52 is curved and the walls of the root canal 52 include a portion 56 which is referred to as the inside of the curve of the root canal 52, and a portion 58 which is referred to as the outside of the curve of the root canal 52.

The tapered tip 42 of the instrument 38 illustrated in FIG. 3 can be described as having a curved profile of rotation which is substantially tangential to the ends, such as end 46, of each of the cutting edges, such as cutting edge 28, at the intersections between the tapered tip 42 and the ends of said cutting edges.

In FIG. 3, the instrument 38 is oriented so that the end 46 of cutting edge 28 is substantially centered and it is the only one of the three ends which can be seen in FIG. 3. It will be understood that the ends of the other cutting edges 24 and 26 will be located at elevation 62 which is the dividing line between the working portion 40 and the tapered tip 42, and will be located at angles of 120° about the axis of the instrument 38 from the end 46.

The tapered tip 42 having a curved profile of rotation as illustrated in FIG. 3 may be formed by taking a standard K-type file 10 such as shown in FIG. 2 having the standard 75° included angle tapered tip 30, and holding the tapered tip against a moving abrasive surface while twisting the instrument 38 about its axis and simultaneously moving the end of the instrument along the desired profile against the moving abrasive surface to form the curved profile of rotation 60 such as shown in FIG. 3.

The tapered tip 42 of instrument 38 includes a reduced diameter cutting means 64 immediately adjacent the ends, such as end 46, of the cutting edges 24, 26 and 28. This reduced diameter cutting means 64 provides a means for automatically cutting a step back in the root canal 52 as the instrument 38 is operated to enlarge the root canal 52.

The reduced diameter cutting means 64 cuts by means of the edges such as 66 and 68 illustrated in FIG. 3 which are formed where the smooth portion of tapered tip 42 intersects with the sides 18, 20 and 22 of the generally triangular shaped shaft. These cutting edges such as 66 and 68 of reduced diameter cutting means 64 are not as sharp as the spiral shaped cutting edges 24, 26 and 28 but they can still cut. The reduced diameter cutting means 64 of tapered tip 42 defines an axially innermost part of the curved profile of rotation 60 of tapered tip 42.

Referring now to FIG. 4, an alternative embodiment of the present invention is there shown and generally designated by the numeral 70.

The instrument 70 has a working portion, the axially forwardmost of which is shown in FIG. 4 and designated by the numeral 72.

The instrument 70 further includes a tapered tip 74 having a length 76.

The tapered tip 74 of instrument 70 includes an axially outermost conical shaped portion 78 having a length 80, and includes an axially innermost frusto-conical shaped portion 82 having a length 84.

This construction of the tapered tip 74 provides a tapered tip having a profile of rotation 86 at least partially defined on each radial side thereof by a plurality of intersecting straight lines such as 88 and 90. The axially innermost part of this profile of rotation 86 which is coincident with the frusto-conical shaped portion 82 is itself frusto-conical in shape.

The axially outermost conical shaped part 78 of tapered tip 74 has an included angle 92 in the range of 60° to 90°. The axially innermost frusto-conical shaped portion 82 has an included angle of substantially less than 75°. The included angle of frusto-conical shaped portion 82 is that angle between diametrically opposed straight sides thereof such as the straight line 90. The included angle of frusto-conical shaped portion 82 is preferably in the range of about 20° to 50°, and most preferably is approximately 35°.

It has been determined that a 35° included angle for frusto-conical shaped portion 82 approximates the shape of the continuously curved tapered tip 42 adjacent the ends of the cutting edges 24, 26 and 28 sufficiently that the instrument 70 with the tapered tip 74 performs in approximately the same manner as the instrument 38 having the continuously curved tapered tip 42.

The conical shaped axially outermost tapered part 78 of tapered tip 74 has a base 94 which has a base diameter approximately one-half of an outside diameter of the working portion 72 at the ends such as end 96 of the cutting edges 24, 26 and 28.

In that regard, it will be appreciated when viewing FIGS. 2, 3 and 4 that when a standard K-type file is modified to have a tapered tip like that shown in either FIGS. 3 or 4, the location of the ends of the cutting edges 24, 26 and 28 is changed since a portion of the cutting edges is removed when creating the longer tapered tip of either FIGS. 3 or 4. Since the working portion of the instruments is itself tapered as previously described, the outside diameter of the working portion of the instrument at the ends of the spiral shaped cutting edges varies slightly as the length of the tapered tip is varied. It has been determined that when the base 94 has a diameter approximately one-half of this outside diameter of the working portion at the ends of the spiral shaped cutting edges, the overall profile of the tapered tip 74 most closely approximates the profile 60 of the tapered tip 42 of FIG. 3.

As illustrated in FIG. 4, the axially outermost tapered portion 78 of tapered tip 74 is immediately adjacent and intersects the axially innermost frusto-conical shaped tapered portion 82 of tapered tip 74.

The axially innermost frusto-conical shaped tapered portion 82 of tapered tip 74 includes a reduced diameter cutting means 98 which is comprised of cutting edges 100 and 102 analogous to the cutting edges 66 and 68 previously described with regard to FIG. 3. This reduced diameter cutting means 98 is entirely a part of the frusto-conical shaped axially innermost tapered portion 82 of tapered tip 74.

The axially innermost frusto-conical shaped portion 82 of tapered tip 74 can be described as having a maximum outside diameter end at elevation 104 immediately adjacent the ends such as end 96 of the spiral shaped cutting edges 24, 26 and 28, and equal in diameter to the outside diameter of the working portion 72 at the ends of the cutting edges 24, 26 and 28. It may also be described as having a minimum outside diameter end 106 coincident with the base 94 of conical shaped portion 78.

METHOD OF MANUFACTURING THE ENDODONTIC INSTRUMENTS OF THE PRESENT INVENTION

The standard K-type endodontic file of the prior art, such as the file 10 illustrated in FIG. 2, is constructed by axially twisting the shaft 12, of polygonal cross-section as seen in FIG. 5, thereby forming on the shaft 12 the working portion 16 having a plurality of rotational bi-directional spiral cutting edges thereon, as seen in FIG. 1.

Then the standard tapered tip 30 having a nominal 75° included angle 32 is formed on the end of the shaft 12 by holding the shaft 12 at an angle of 37½° to a moving abrasive surface while rolling the instrument 10 about its longitudinal axis, thus grinding the 75° included angle conically shaped tip 30 on the instrument 10.

The improved instrument 38 illustrated in FIG. 3 having the continuously curved tapered tip 42 has been constructed by modifying a conventional prior art K-type file 10 by regrinding the tapered tip thereof.

This has been done by utilizing an oscillating flat abrasive surface and holding the endodontic instrument by hand while engaging the tip thereof with the oscillating surface in a controlled manner. The tip is originally held so that the points such as 34 and 36 are engaged with the oscillating abrasive surface to grind those points off and lengthen the tapered tip such as shown in FIG. 3 so that the tapered tip 42 is substantially tangential to the cutting edges 24, 26 and 28 at its intersection therewith. The instrument 38 is rotated about its longitudinal axis while the tip is being held against the oscillating abrasive surface. Then, while continuing to rotate the instrument 38 about its longitudinal axis, the angle of the axis of the instrument 38 to the oscillating flat abrasive surface is steadily increased from approximately 0° to approximately 90° thus grinding the curved profile of rotation 60 shown in FIG. 3 on the tip of the instrument.

While this continuously curved tapered tip 42 as shown in FIG. 3 is preferred since it eliminates entirely the points at the intersection of the tapered tip with the ends of the cutting edges 24, 26 and 28, it will be appreciated that the manual forming of these continuously curved tapered tips is a tedious operation. Also, it will be appreciated that the automated machinery to construct such curved tips would be rather complex.

The alternative embodiment of FIG. 4 provides an approximation of the continually curved surface shown in FIG. 3, which is much easier to form on the instrument.

The tapered tip 74 of the instrument 70 shown in FIG. 4 may be formed by taking a conventional prior art K-type file such as the file 10 shown in FIG. 2, and holding the file so that its longitudinal axis is at an angle of 17½° to a flat oscillating surface and then holding the instrument against the tapered surface and rolling it about its longitudinal axis so as to grind the sharp points such as 34 and 36 off of the instrument and form the frusto-conical shaped axially innermost portion 82 of tapered tip 74 shown in FIG. 4.

By either of these methods, the sharp points normally present at the intersection of a standard 75° included angle conically tapered tip with the spiral cutting edges of a K-type instrument such as the instrument 10 shown in FIG. 2 are eliminated.

OPERATING METHODS OF THE PRESENT INVENTION

Figure 8:
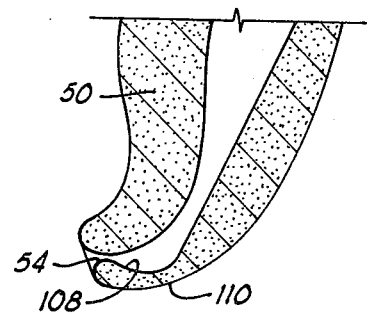
FIG. 8 is a cross-section elevation somewhat schematic view of a human tooth which has been cleaned and enlarged with standard K-type endodontic instruments of the prior art in such a fashion that significant lateral transportation of the instruments has occurred near the apex of the root canal.

As previously discussed, a serious problem is encountered when utilizing standard K-type files such as the instrument 10 shown in FIG. 2 to clean and enlarge a curved root canal such as the root canal 50 illustrated in FIG. 7. As larger and larger sizes of instruments are used to enlarge the canal, a ledge such as designated by the numeral 108 in FIG. 8 is often created due to the tendency of the standard K-type file to cut toward the outside curve 58 of the root canal 52 at the forwardmost extent of the file. Many examples of such problems are described and illustrated for example in the text Ingle and Beveridge, *Endodontics*, at Chapter 3, pages 101–215 entitled "Endodontic Cavity Preparation" (1976).

I have determined that the primary cause of this lateral transportation of prior art K-type files such as the file 10 of FIG. 2 is the presence of the sharp points such as 34 and 36 which create very high stress concentrations applied to the tooth material along the outside curve of the root canal 52. These sharp points gouge the tooth material causing a ledge along the outside curve 58.

As larger and larger sizes of the standard K-type files are utilized, a large ledge such as ledge 108 is created, and if allowed to go to the extreme, the instruments will actually perforate the side of the tooth root 50 at approximately the location 110 shown in FIG. 8.

With the improved endodontic instrument of the present invention, such as either the instruments 38 or 70 shown in FIGS. 3 and 4, a drastically improved result is provided as compared to the prior art instrument 10.

By eliminating the sharp points at the ends of the spiral cutting edges, the force exerted by an axially outermost part of the working portion and by the reduced diameter cutting means of the tapered tip of either the instrument 38 or 70 of the present invention is spread over a much larger area of tooth material as compared to the prior art file 10, and thus no sharp ledges are created.

Furthermore, the elongated tapered shape of the tapered tips 42 and 74 causes the tapered tip to be wedged into an uncut portion of the root canal as the instrument is advanced into the root canal 52, and thereby substantially centers a forwardmost part of the working portion of the instrument in the root canal 52 thus further aiding the instrument to cut tooth material from both the inside 56 and the outside 58 of the curve of the root canal 52.

Lateral transportation of the instrument when cutting a curved root canal is very much reduced as compared to an otherwise similar instrument having a standard 75° included angle tapered tip such as illustrated in FIG. 2 of the application.

Figure 9:
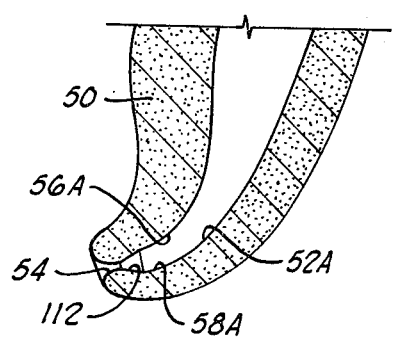
FIG. 9 is a cross-section elevation somewhat schematic view of a root canal of a human tooth which has been cleaned and enlarged utilizing the improved endodontic instruments of the present invention.

By using the improved instruments 38 or 70 of the present invention, the root canal 52 is cleaned and enlarged to a final shape such as illustrated in FIG. 9 wherein the enlarged root canal is designated 52A, and the enlarged inside curve and outside curve of the root canal are designated as 56A and 58A, respectively.

Furthermore, the tapered reduced diameter cutting means 64 or 98 of the instruments 38 or 70, respectively, automatically cut a step back in the root canal 52A. Such a step back is schematically illustrated in FIG. 9 and designated by the numeral 112. This step back 112 is a surface facing away from the apex 54 of the root canal 52A and it provides a restriction against which filler material such as gutta percha may be compacted.

With prior art instruments such as the file 10 illustrated in FIG. 2, it is generally necessary to decrease the depth to which successively increasing diameter files are inserted in order to form a step back. Prior art procedures for forming step backs using standard K-type files are described in the Ingle and Beveridge text cited above, and are illustrated at page 200 thereof.

The present invention, however, automatically provides a step back feature due to the provision of the reduced diameter cutting means.

As will be understood by those skilled in the art, there are a number of various types of cutting strokes utilized by endodontists. These cutting strokes can generally be described as filing or reaming. A filing stroke refers to the axial reciprocation of the cutting instrument along the length of the root canal without rotating the instrument. Thus the edges file the interior walls of the root canal. A reaming stroke refers to the use of rotational motion of the instrument by rotating it about its longitudinal axis.

One variation of a reaming stroke, which is itself a part of the prior art, includes the use of reciprocating rotational motion wherein the file is rotated clockwise through an angle in the range of about 90° to 270° so as to advance the instrument into a portion of the root canal previously uncut by that particular instrument. Then while holding a downward pressure on the instrument to keep it from backing out of the root canal, the instrument is rotated counterclockwise through an angle of at least 120° (the angle between cutting edges) and the material from the walls of the root canal is actually cut on this counterclockwise rotational stroke. Then the instrument is again rotated clockwise to again advance it to yet another uncut portion of the root canal, and then another counterclockwise motion cuts material from that portion of the root canal. The instrument is alternately rotated clockwise to advance it into the root canal and then counterclockwise to cut material from the root canal. A final cutting stroke is typically made with one to two revolutions clockwise to aid in debris removal once the desired portion of the root canal has been cut with counterclockwise cuts.

I have determined that this operating stroke of rotationally reciprocating the instrument to alternately advance the instrument in the root canal and then cut material from the root canal is preferable for use with the improved endodontic instruments 38 and 70 shown in FIGS. 3 and 4. Such a cutting stroke is itself, however, a part of the prior art as I have used it for many years with standard K-type files such as the file 10 shown in FIG. 2.

The improved endodontic instrument may also be used with a filing stroke where the instrument is advanced, preferably by clockwise rotation, then axially withdrawn to cut the tooth material.

One other significant advantage provided by the present invention as compared to prior art systems and methods is that there is no need to precurve the instruments 38 or 70 when cleaning a curved root canal. A very common prior art method of dealing with curved root canals is to bend or precurve the instrument to approximate the curvature of the canal prior to insertion of the instrument into the root canal. Such precurved instruments are then most often used with a solely axially reciprocating filing stroke, because when a precurved instrument is rotated the cyclic bending stresses often lead to breakage of the instrument. The present invention provides an instrument which can readily clean and enlarge a curved root canal while using a rotational cutting stroke.

TEST RESULTS

Laboratory tests were conducted utilizing instruments such as the instrument 38 illustrated in FIG. 3 and comparing their performance to otherwise similar instruments having a standard tip 30 such as illustrated in FIG. 2.

Testing was performed with acrylic canal models such as those designated as Model 001 available from Richard W. Pecina & Associates, Inc., Waukegan, Illinois. These models are formed from clear acrylic material and each model has a similar elongated tapered canal cast therein to simulate a root canal of a human tooth. The canals are curved to simulate a curved root canal.

Utilizing the standard K-type files such as the file 10 illustrated in FIG. 2, lateral transportation typically began at instrument size 35 and became significant by size 40 or 45. It was essential with those standard instruments to utilize a step back procedure wherein the instruments of increased diameter were inserted to a reduced depth in the tooth, in order to prevent lateral transportation and creation of a ledge.

Files such as file 38 shown in FIG. 3 of the application were then utilized on substantially identical test blocks and it was found that canals could be enlarged through file size 55 along the entire length of curvature to form an enlarged canal such as illustrated in FIG. 9 without any significant lateral transportation. It was not required to use a step back procedure.

Subsequently, after developing the alternative embodiment shown in FIG. 4, it was possible to produce instruments in sufficient quantity to allow clinical testing. The instruments 70 shown in FIG. 4, when utilized in clinical testing on live patients, have been found to produce superior instrument tip control and to produce apparently the same results clinically as were observed in the acrylic laboratory models.

The results of these tests conclusively show that endodontic instruments having the modified tips of the present invention such as instruments 38 and 70 shown in FIGS. 3 and 4, provide dramatically improved performance when cleaning and enlarging curved root canals.

The problem of lateral transportation of the instrument in the curved root canal is substantially eliminated and the canals may be uniformly enlarged throughout their entire length so as to provide a superior root canal preparation for filling.

THE IMPROVED TIP DESIGN OF THE PRESENT INVENTION IS APPLICABLE TO OTHER CROSS-SECTION SHAPES

As disclosed above, the preferred embodiment of the present invention utilizes a file constructed by axially twisting a triangular shaped shaft to form a file with three spiral rotational bi-directional cutting edges thereon. It will be understood, however, that the invention is equally applicable and useful on endodontic instruments having other cross-sectional shapes.

Several other such shapes are presently known in the art. One is an instrument constructed by axially twisting a shaft having a square cross-sectional shape so that it has four spiral rotationally bi-directional cutting edges. Another instrument to which the present invention is applicable is an instrument having a cross-section in the shape of an oblique parallelogram such as is disclosed and described in U.S. Pat. No. 4,260,379 to Groves et al. Further, U.S. Pat. No. 1,067,015 to Fowler shows an instrument having a rectangular shape cross-section.

Generally, any instrument which is constructed by axially twisting a shaft of polygonal cross-section so as to form a plurality of spiral rotationally bi-directional cutting edges thereon may be improved by the use of the tapered tip of the present invention.

Thus it is seen that the apparatus and methods of the present invention readily achieve the ends and advantages mentioned as well as those inherent therein. While certain preferred embodiments of the present invention have been illustrated for the purposes of the present disclosure, numerous changes in the arrangement and construction of parts and steps may be made by those skilled in the art, which changes are encompassed within the scope and spirit of the present invention as defined by the appended claims.

What is claimed is:

1. An endodontic instrument, comprising:
    a tapered working portion defined on a flexible shaft, said working portion including a plurality of spiral rotationally bi-directional cutting edges thereon; and
    a tapered tip defined on said flexible shaft and intersecting an end of each of said cutting edges of said working portion, said tapered tip having a greater angle of taper than said tapered working portion, said tapered tip being shaped such that sharp cutting points which are normally present at an intersection between said ends of each of said cutting edges and a standard 75° included angle conically tapered tip are substantially eliminated so that lateral transportation of said instrument when cutting a curved root canal is reduced as compared to an otherwise similar instrument having a standard 75° included angle conically tapered tip intersecting said ends of said cutting edges.

2. The instrument of claim 1, wherein:
    said tapered tip is continuously tapered from a forwardmost end thereof to said ends of said cutting edges.

3. The instrument of claim 2, wherein:
    said continuously tapered shape of said tapered tip provides a means for wedging said tapered tip into an uncut portion of a root canal as said instrument is advanced into said root canal and for thereby substantially centering a forwardmost part of said working portion of said instrument in said root canal and causing said instrument to cut tooth material from both an inside and an outside of a curve of said root canal.

4. The instrument of claim 1, wherein:
    said tapered tip has a profile of rotation at least partially defined on each radial side by a plurality of intersecting straight lines.

5. The instrument of claim 4, wherein:
    an axially innermost part of said profile is frusto-conical in shape.

6. The instrument of claim 1, wherein:
    said tapered tip has a curved profile of rotation which is substantially tangential to said ends of each of said cutting edges at the intersections between said tapered tip and said ends of said cutting edges.

7. The instrument of claim 1, wherein:
said tapered tip includes an axially innermost tapered portion immediately adjacent said ends of said cutting edges, said innermost tapered portion being generally frusto-conical in shape and having an included angle of substantially less than 75°.

8. The instrument of claim 7, wherein:
said included angle of said frusto-conical shaped innermost tapered portion is approximately 35°.

9. The instrument of claim 7, wherein:
said tapered tip includes an axially outermost tapered portion which is conical in shape and has an inclined angle in the range of 60° to 90°.

10. The instrument of claim 9, wherein:
said conical shaped axially outermost tapered portion has a base diameter approximately one-half of an outside diameter of said working portion of said shaft at said ends of said cutting edges.

11. The instrument of claim 9, wherein:
said axially outermost tapered portion is immediately adjacent and intersects said axially innermost tapered portion of said tapered tip.

12. The instrument of claim 1, wherein:
said working portion of said flexible shaft is generally polygonal in cross-section.

13. The instrument of claim 12, wherein:
said cross-section of said working portion of said flexible shaft is generally shaped as an equilateral triangle.

14. The instrument of claim 1, wherein:
said working portion of said flexible shaft is formed by twisting a blank which is polygonal in cross-section, said cutting edges being defined at intersections of adjacent sides of said polygonal cross-section.

15. The instrument of claim 14, wherein:
said cross-section of said blank is shaped as an equilateral triangle.

16. The instrument of claim 1, wherein:
said tapered tip includes a reduced diameter cutting means immediately adjacent said ends of said cutting edges.

17. The instrument of claim 16, wherein:
said reduced diameter cutting means provides a means for automatically cutting a step back in a root canal as said instrument is operated to enlarge said root canal.

18. The instrument of claim 16, wherein:
said tapered tip includes an axially innermost tapered portion immediately adjacent said ends of said cutting edges, said innermost tapered portion being generally frusto-conical in shape and having an included angle of substantially less than 75°; and
said reduced diameter cutting means is entirely a part of said frusto-conical shaped axially innermost tapered portion of said tapered tip.

19. The instrument of claim 16, wherein:
said tapered tip has a curved profile of rotation which is substantially tangential to said ends of said cutting edges at the intersection between said tapered tip and said ends of said cutting edges, said reduced diameter cutting means of said tapered tip defining an axially innermost part of said curved profile.

20. An endodontic instrument, comprising:
a working portion defined on a flexible shaft, said working portion including a plurality of spiral rotationally bi-directional cutting edges thereon; and
a tapered tip defined on said flexible shaft and intersecting an end of each of said cutting edges of said working portion, said tapered tip including:
an axially outermost tapered portion which is substantially conical in shape and has an included angle in the range of 60° to 90°; and
an axially innermost tapered portion which is substantially frusto-conical in shape and has an included angle of substantially less than 75°.

21. The instrument of claim 20, wherein:
said axially innermost tapered portion of said tapered tip has a maximum outside diameter end immediately adjacent said ends of said cutting edges and equal in diameter to an outside diameter of said working portion of said shaft at said ends of said cutting edges; and
said conical shaped axially outermost tapered portion of said tapered tip has a base coincident with a minimum outside diameter end of said frusto-conical shaped axially innermost tapered portion.

22. The instrument of claim 21, wherein:
said base of said conical shaped axially outermost tapered portion of said tapered tip has a diameter of approximately one-half of said outside diameter of said working portion of said shaft at said ends of said cutting edges.

23. The instrument of claim 20, wherein:
said included angle of said frusto-conical shaped axially innermost tapered portion of said tapered tip is in the range of about 20° to 50°.

24. The instrument of claim 23, wherein:
said included angle of said frusto-conical shaped axially innermost tapered portion of said tapered tip is approximately 35°.

25. The instrument of claim 20, wherein:
said working portion of said flexible shaft is generally polygonal in cross-section.

26. The instrument of claim 25, wherein:
said cross-section of said working portion of said flexible shaft is generally shaped as an equilateral triangle.

27. The instrument of claim 20, wherein:
said working portion of said flexible shaft is formed by twisting a blank which is polygonal in cross-section, said cutting edges being defined at intersections of adjacent sides of said polygonal cross-section.

28. The instrument of claim 27, wherein:
said cross-section of said blank is shaped as an equilateral triangle.

* * * * *